United States Patent
Faizan et al.

(10) Patent No.: US 12,415,005 B2
(45) Date of Patent: Sep. 16, 2025

(54) SELF SANITIZING DOOR HANDLE WITH PROTECTIVE COVER

(71) Applicant: Mirza Faizan, Irving, TX (US)

(72) Inventors: Mirza Faizan, Irving, TX (US); Mirza Rizwan, Patna (IN); Maleeha Khan, Frisco, TX (US); Imaan Moosa, Frisco, TX (US); Inaya Sheikh, Plano, TX (US); Mahum Rana, Plano, TX (US); Laiba Mehmood, Frisco, TX (US); Ayaan Mehmood, Frisco, TX (US); Aamena Baig, Irving, TX (US); Ayesha Baig, Irving, TX (US); Deen Sheikh, Plano, TX (US)

(*) Notice: Subject to any disclaimer, the term of this patent is extended or adjusted under 35 U.S.C. 154(b) by 1140 days.

(21) Appl. No.: 17/339,305

(22) Filed: Jun. 4, 2021

(65) Prior Publication Data
US 2022/0387639 A1    Dec. 8, 2022

(51) Int. Cl.
*A61L 2/10* (2006.01)
*E05B 1/00* (2006.01)

(52) U.S. Cl.
CPC ............. *A61L 2/10* (2013.01); *E05B 1/0069* (2013.01); *A61L 2202/11* (2013.01); *A61L 2202/14* (2013.01)

(58) Field of Classification Search
CPC .................. A61L 2/10; E05B 1/0069
See application file for complete search history.

(56) References Cited

U.S. PATENT DOCUMENTS

| | | | |
|---|---|---|---|
| 2012/0176241 A1* | 7/2012 | Pasch | A61L 2/10 250/492.1 |
| 2015/0360606 A1* | 12/2015 | Thompson | B60Q 3/283 362/490 |

FOREIGN PATENT DOCUMENTS

DE    102011001094 A1 *  9/2012  ............ A61L 2/10

OTHER PUBLICATIONS

English translation of DE-102011001094-A1 (Year: 2012).*

* cited by examiner

*Primary Examiner* — Sean E Conley (57) ABSTRACT

The present invention relates to a self sanitizing door handle and a method of operating the same. The door handle comprising: a soft glass hollow membrane; one or more connectors; a central rod; and a plurality of lights on said central rod inside said hollow membrane protectively covered by said one or more connectors in an active state of sanitization in said self sanitizing door handle. Furthermore, the door handled is a self powered door handle based on a spring and rail with turbines mechanism which contracts and relaxes to generate desired amount of power required to drive the door sanitization system in the self sanitizing door handle.

7 Claims, 7 Drawing Sheets

SELF SANITIZING DOOR HANDLE WITH PROTECTIVE COVER

TECHNICAL FIELD

The invention relates to a door handle sanitizer unit. More specifically, the invention relates to ultraviolet light-based door handle sanitizer unit. Furthermore specifically, the invention relates to a self powered ultraviolet light based door handle sanitizer unit.

BACKGROUND OF THE INVENTION

In general, it has been noted that every person is exposed to enormous microbes on a daily basis. These microbes may include viral and bacterial diseases and contribute to spreading communicable diseases. Diseases may be transmitted by direct contact when an infected person touches another person or by indirect contact when there is no direct person-to-person contact. Most often, indirect transfer of disease occurs when an infected person touches a surface and leaves behind microbes on the surface. An uninfected person subsequently touches the same surface and the microbes adhere to the skin. Examples of communicable diseases that may be spread in this way are chicken pox, common cold, conjunctivitis (pinkeye), Hepatitis A and B, herpes simplex (cold sores), influenza, measles, rhino viruses, and coronavirus.

Further, according to the recent census over 1 million in the United States alone are hospitalized from COVID-19 complications and 80,000 people died from COVID-19. The health departments also reports that the COVID-19 virus can survive on inanimate surfaces for 2 to 8 hours. To prevent transfer of COVID-19 from these surfaces, the health departments recommends washing hands often and the use of chemical germicides such as wipes or gels containing alcohol.

However, these preventative measures are impractical to use every time a potentially contaminated surface is touched. For example, most people wash their hands after using bathroom facilities, and then touch the doorknob upon leaving the bathroom. The doorknob may contain bacterial diseases left by a prior bathroom user who did not, or inadequately, washed their hands. Generally, a person does not wash their hands again immediately after leaving the bathroom. Similarly, doorknobs in any public space are touched by numerous people infected with contagious diseases. It is not practical for every person using the public space to wash their hands or use a sanitizer after every contact with a doorknob. In a research, it was found that if one person enters a mid-size office of 500 employees, within 4 hours, 80% of employees get infected. Furthermore, manually cleaning of the door handles does not provide significant results due to the usage by large mass.

Some prior art methods suggest covering a handle of a door so a person opening the door can avoid direct contact with the handle. Covering a door handle, while effective in preventing a person from contacting the door handle during operation of the door, does little to clean or disinfect the door handle. Furthermore, the cover then becomes a source of contamination, germs, bacteria and the like. Moreover the presently available other alternates of sanitization does not provide an effective solution to the issue of sanitization. Therefore, there is a need for efficiently and effectively sanitizing the handle of a door.

Hence there is an utmost need to build ultraviolet light based self sanitizing door handle.

SUMMARY OF THE INVENTION

An embodiment is directed to a self sanitizing door handle. The door handle comprising: a soft glass hollow membrane; one or more connectors; a central rod; and a plurality of lights on said central rod inside said hollow membrane protectively covered by said one or more connectors in an active state of sanitization in said self sanitizing door handle. Furthermore, the door handled is a self powered door handle based on a spring and rail with turbines mechanism which contracts and relaxes to generate desired amount of power required to drive the door sanitization system in the self sanitizing door handle.

In addition to one or more of the features described above or below, or as an alternative, wherein the self powered mechanism is based on an assembly of spring and rail with plurality of turbines.

In addition to one or more of the features described above or below, or as an alternative, the self sanitizing door handle comprising a light indication unit configured to reflect a status of the plurality of lights inside said soft glass hollow membrane.

In addition to one or more of the features described above or below, or as an alternative, wherein the one or more connectors are interlocking connectors configured to act as a shield cover during a working state of said plurality of lights in said soft glass hollow membrane.

In addition to one or more of the features described above or below, or as an alternative, wherein the self sanitizing door handle further comprising an outer covering of aluminium.

In addition to one or more of the features described above or below, or as an alternative, wherein the self sanitizing door handle further comprising one or more sensors configured to detect presence of one or more users.

In addition to one or more of the features described above or below, or as an alternative, wherein self sanitizing door handle comprising a control circuit for causing the UV-C disinfectant to be conveyed to the handle in intervals, wherein the intervals are responsive to an external condition and the control circuit if free of any manual activation.

An embodiment is directed to method of operating the self sanitizing door handle.

An exemplary embodiment may be directed to an ultraviolet light based self sanitizing door handle. The self sanitizing door handle comprises a thermal detector or a sensor that may sense a presence of human being. The protective casing also includes an automatic ultra violet light emission assembly. The UV emission assembly triggers when the one or more connectors are in working state and are completely closed.

Alternatively, the self sanitizing door handle further comprises a thermal detector or a sensor that may sense a presence of human being or a voice enabled sensor to detect human voice. The protective casing also includes an automatic ultra violet light emission assembly. The assembly may further comprise one or more sensors to perform auto detections and auto trigger functions. Furthermore, the door may be wirelessly connected with a secured system. The door of such a secured system may have an eye sensor or a voice enabled sensor that may match the previously stored data with the voice and eye of the user, and upon verification, enables the user to reach to the handle of the door.

Objects of the Invention

The object of the disclosed invention is to provide a self sanitizing door handle.

Yet another object of the disclosed invention is to provide ultraviolet light based door handle.

Yet another objective of the invention is to provide the ultraviolet light based door handle that works in closed environment.

Yet another objective of the invention is to provide an ultraviolet light based door handle that detects human presence.

Yet another objective of the invention is to provide a self powered ultraviolet light based door handle to kill germs and viruses from the door handle.

Yet another objective of the invention is to provide a self powered sensor based automatic ultraviolet light based door handle to kill germs and viruses from the door handle.

Yet another objective of the invention is to provide a self powered sensor based automatic voice enabled ultraviolet light based door handle to kill germs and viruses from the door handle.

Yet another objective of the invention is to provide a secured self powered eye detection sensor based automatic ultraviolet light based door handle to kill germs and viruses from the door handle.

BRIEF DESCRIPTION OF THE DRAWINGS

The accompanying drawings illustrate various embodiments of systems, method_s, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION OF DRAWINGS

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

It is noted that various connections are set forth between elements in the following description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

Figure 1:
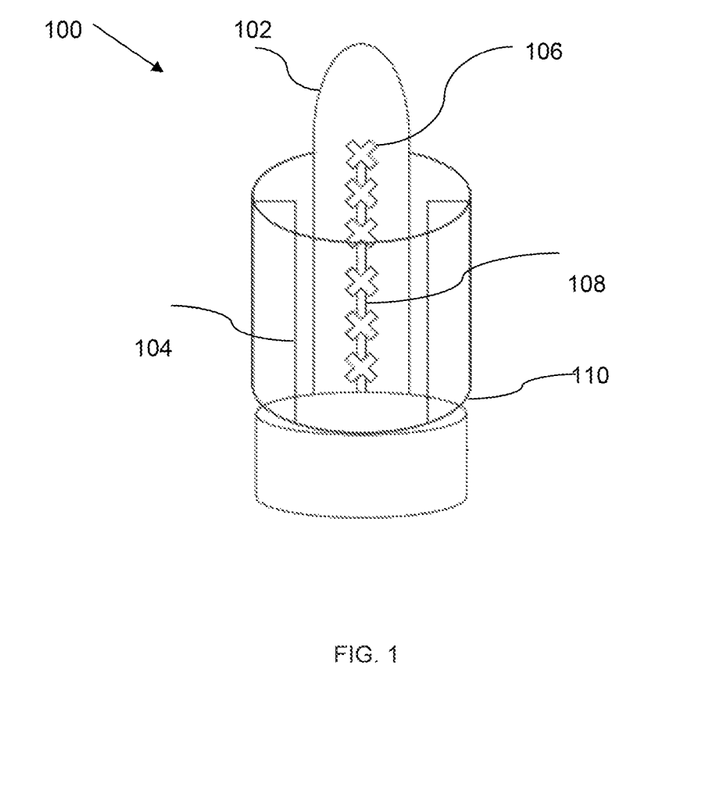
FIG. 1 is a self sanitizing door handle in a closed environment in which various embodiments may be implemented.

FIG. 1 is a self sanitizing door handle in a closed environment in which various embodiments may be implemented.

FIG. 1 is a self sanitizing door handle in a closed environment in which various embodiments may be implemented. FIG. 1 shows self sanitizing door handle 100 that includes a soft glass tube 102, a connector 104, an ultra violet rays light 106, a central rod 108, and a base 110. Various devices in the system environment 100 may be interconnected. The self sanitizing door handle 100 is closed in this instance. Hence, the UV source is in closed circuit and may operate in pre-determined interval, after the first instance of operation.

The soft glass tube 102 may corresponds to an outer shell of the handle. The entire handle may be made up of multiple components and materials thereof. The soft glass tube may be an unbreakable glass tube. The soft glass tube may be hollow from inside so that UVC LED lights are inserted Furthermore, the glass tube may be made in such a manner that the UV-C lights present inside the glass tube may enable to emit the UV-C to the outer layer of the door handle and thereby kills one or more germs/viruses present on the handle of the door.

The connector 104 may be an interlocking enabled connector. The connector may be contracted when the handle of the door may not be in a state of red or orange light. Hence, the connector may be contracted when the UV-C light radiations may not be activated and the door may be in a usable state, i.e green light.

The UV-C lights 106 may correspond to ultra violet emitting lights. The number of lights inside the door handle may be based on the length and the user requirement. The user may alter the number of lights in functional state as per the frequency of usage. In an embodiment, an internal protection circuit may be placed along with the UV-C lights, that may protect the lights and moreover from any power issues.

The central rod 108 may be the inner most part of the door handle. The central rod may be made up of aluminium or a wooden based material upon which the UV-C lights are placed. The placement of the UV-C lights on the central rod may be based as per the need of the user. The user requirement may be based on frequency of usage of the door handle or strict sanitization requirement for a longer time.

In an embodiment of the present invention, the central rod 108 may have additional one or more connections for placing UV-C lights in a staggered manner.

The base 110 of the door handle may be made up of any metallic material to provide strength to the overall door handle assembly. The top portion of the door handle may also be alike the base of the door handle. In an embodiment, the upper base of the door may contain a camera. The camera may be configured to capture the image of the user accessing the door. This captured photo may be used further for contact tracing using the microprocessor.

Figure 2:
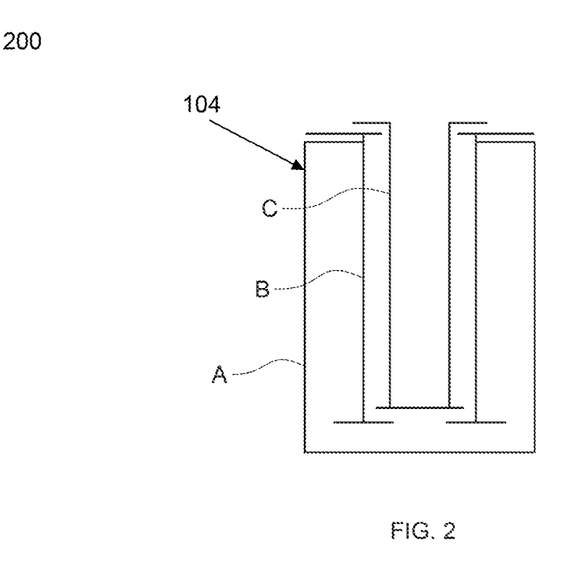
FIG. 2 is a position of connectors in an operative mode of self sanitizing door handle.

FIG. 2 illustrates a position of connectors in an operative mode of self sanitizing door handle.

As shown a detail instance of the connector 104, as 200. The connector 104 may include a plurality of parts that may be configured to cover the handle of the door during the process of sanitization.

The connector may be in an inter locking mechanism, wherein it may have parts exemplary as A, B, and C. These parts may be interlocked via a connector. Hence at this stage, the connectors are contracted and the state of the door is not being actively sanitized.

Figure 3:
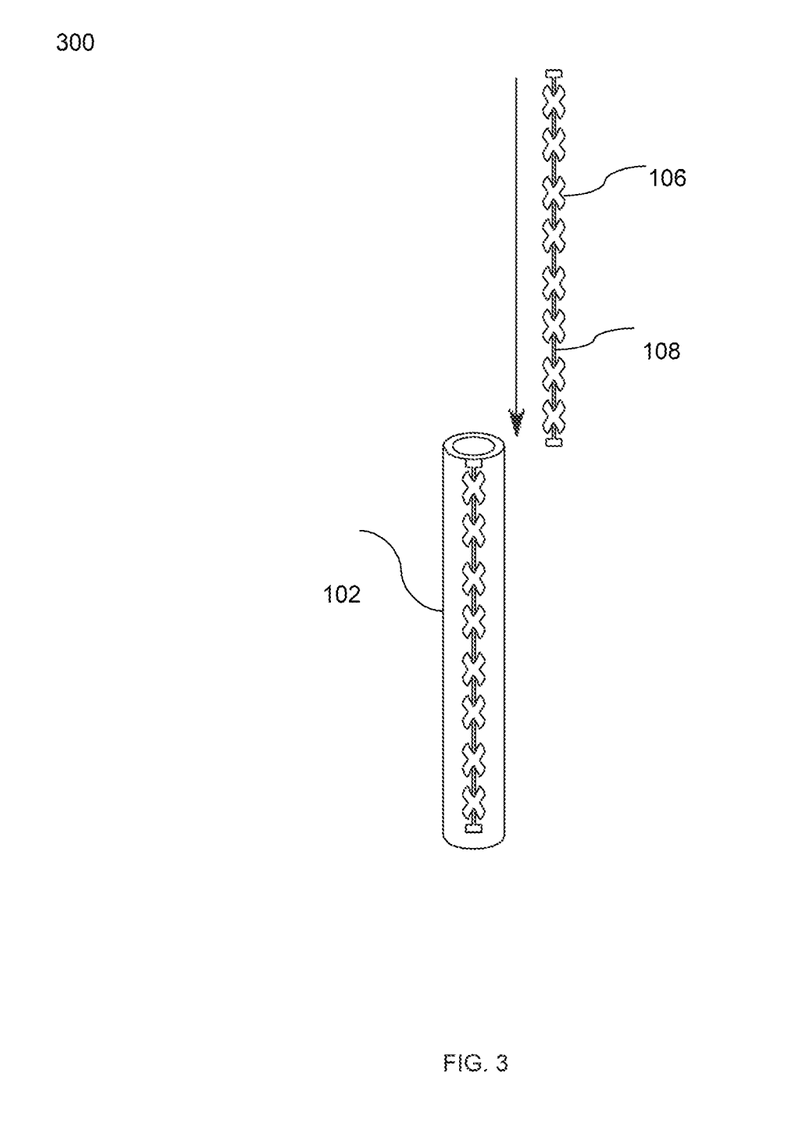
FIG. 3 is an inside configuration of soft glass, in accordance with at least one embodiment.

FIG. 3 is an inside configuration of soft glass, in accordance with at least one embodiment.

There is shown in 300, that the UV-C lights 106 may be placed inside the soft glass tube 102 over the central rod 108. The UV-C lights may be placed up to four sides of the central rod. In an embodiment, the number of lights may be determined at initial installation state based on the requirements and dimensions of the door handle.

Figure 4:
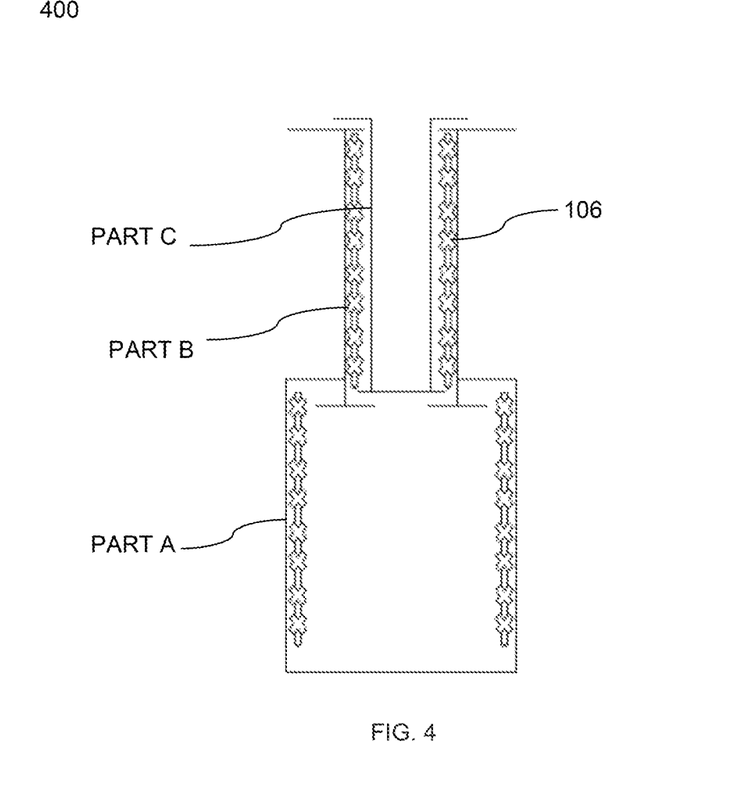
FIG. 4 is a position of UVC lights inside the connectors, in accordance with at least one embodiment.

FIG. 4 is a position of UVC lights inside the connectors, in accordance with at least one embodiment.

In 400, there is shown that the position of UVC lights 106, covered by the connectors, to ensure that the lights do not harm the human, and the rays emitted by the lights upon activation, kills the bacteria and virus over the glass door handle. These connector's acts as a shield or a protective covering at the time when the circuit is closed and the sanitization is taking place. Hence it may acts as a protective cover to the self sanitizing door handle. Furthermore, the UV-C 106 lights may be placed between each layer of the interlocking mechanism.

Figure 5:
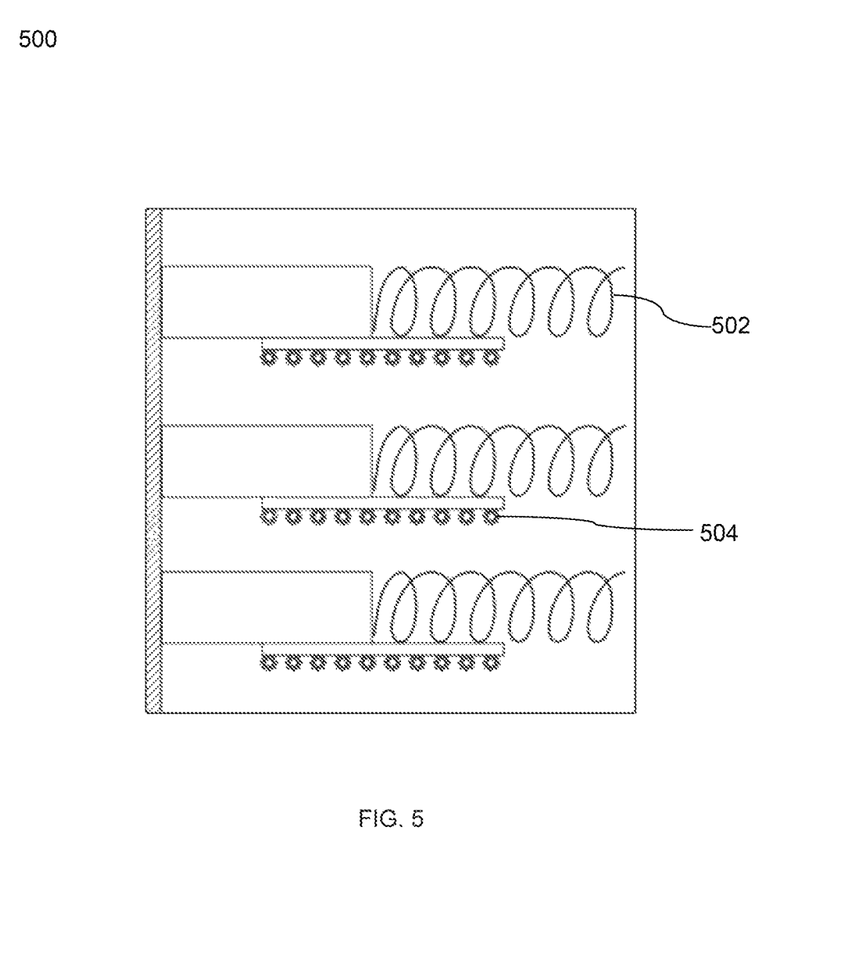
FIG. 5 is a configuration of external battery system to power the self sanitizing door handle, in accordance with at least one embodiment.

FIG. 5 is a configuration of external battery system to power the self sanitizing door handle, in accordance with at least one embodiment.

There is shown in 500, that the Self sanitizing door handle with protective cover may be powered with an external battery system, which may operate based on a self energy generation technique. The technique may be based on the movement of the spring 502 along with the rail and turbine combination 504.

In an embodiment, the movement of the door causes the spring to stretch and compress. As a result of this, the rail with the turbines moves and energy is thereby generated for the handle. Hence, the system may be powered by a dynamo attached to the door. This electricity is then stored in a battery to be used by the system.

Figure 6:
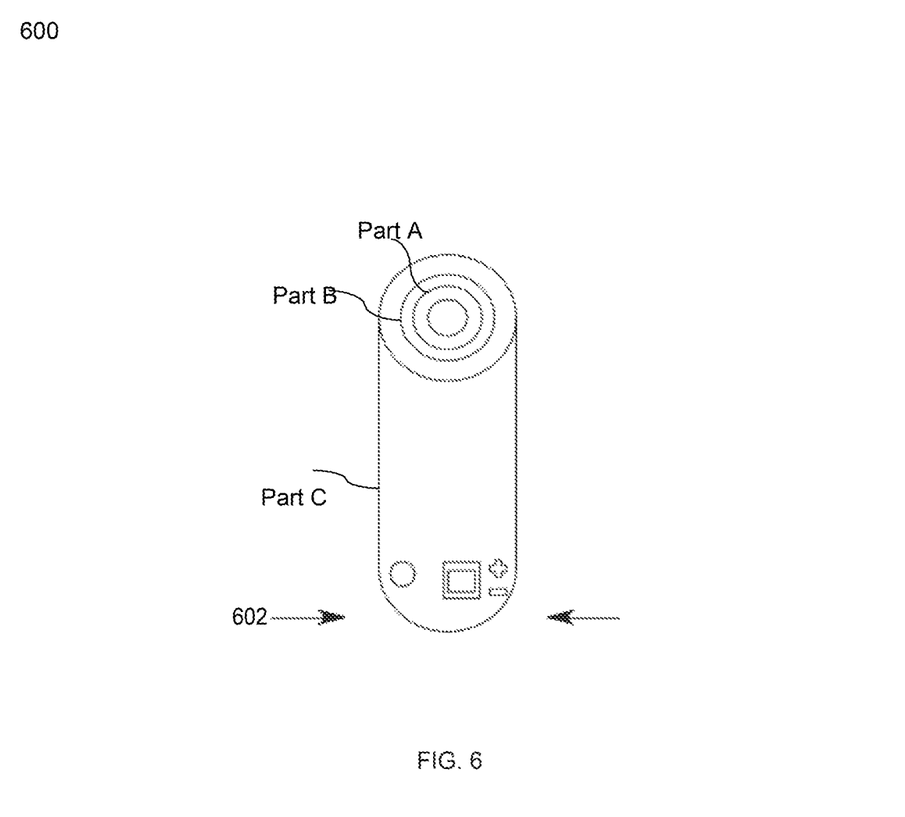
FIG. 6 illustrates a position of connectors in a non-operative mode of self sanitizing door handle, in accordance with at least one embodiment.

FIG. 6 illustrates a position of connectors in a non-operative mode of self sanitizing door handle, in accordance with at least one embodiment.

As shown in 600, that parts of connectors are shown when they are in collapsed state. At this moment the door handle may be ready for use by the user. Furthermore, at this stance he door is not being sanitized and the sanitization was over prior to retraction of the connectors.

Furthermore, there is shown an indicator 602, that may correspond to a light based alarming feature and the light may be operative in multiple modes as Green, Red or Yellow. The green light shows that the door is sanitized and is ready to use. The yellow may indicate that the door is used by a user and is getting prepared to be reused for opening the door. Furthermore, the red light shows that the door is not sanitized and the user should wait for the door handle to get sanitize before the use.

Additionally in an embodiment of the present invention, the Self sanitizing door handle may comprise an adjustable interval trigger mechanism. The adjustable interval system may be configured to operate the auto sanitization of the door after a pre determined time intervals. The time interval may be a user defined time interval as per the frequency of the use of opening the door.

The adjustable intervals may be configured in an automatic manner or may be a user driven. The automatic time intervals may be pre-determined time intervals that may be adjusted by the controller. The controller may be communicatively coupled with the door handle.

Figure 7:
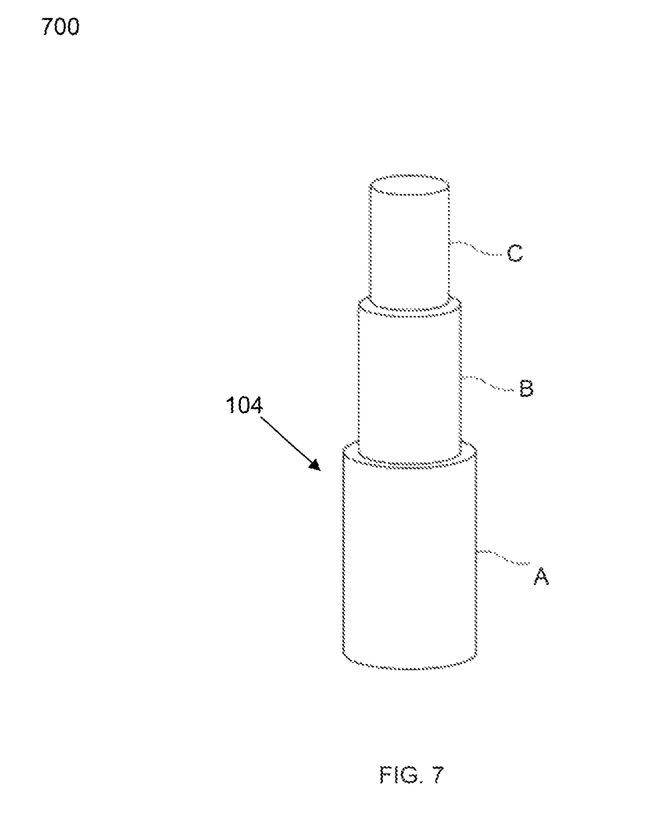
FIG. 7 illustrates the position of connectors in a covering state of interlocking in accordance with at least one embodiment.

FIG. 7 illustrates the position of connectors in a covering state of interlocking in accordance with at least one embodiment.

As shown in 700, the connector is shown in extended state. At this point the handle being sanitized by the UV-C lights and hence the entire glass door may be covered by the connectors in extended mode. Hence, the interlocking parts of the connector may act as a covering mechanism to ensure that the harmful rays do not comes out and impact the user. Furthermore, the interlocking parts may be of varied lengths and depends on the overall length of the UV-C lights rod placed inside the soft glass tube.

In an embodiment of the present invention, the self sanitizing door may comprise a remotely connected controller. The controller may include a microprocessor (not shown) and associated memory. The memory may store operational parameters of the unit, as well as software to control operation of the door. The memory may further store one or more pre-scanned retina images and/or one or more recorded voices of the one or more user, which may generally use the door handle to access the premises. The microprocessor may perform operations according to the software using the operational parameters as well as other parameters or information obtained by the controller.

In an exemplary scenario for self sanitizing door handle with protective cover, the door handle may be an ultraviolet light based door handle, in accordance with at least one embodiment. In this, when the user has to access some door by the handle, then the user notices the light indication on the door handle to alert the user. If the light is green, then the user may push the handle as it is already sanitized, but if it is in red or orange color then the user may have to wait for the door handle alert light to become green in color. Once green the user may use the door handle to get into the premises. Hence, by a pre determined time interval configured processor the UV source becomes activated to emit UV rays or light, which kills the germs or viruses that might have been present on the handle of the door due to the touch of the user, who had recently used to access the premises.

In an embodiment, the door handle may be connected with the door by using any mechanical means, as nuts and bolts.

In an embodiment of the present invention, a method may be disclosed. The method may be configured to enable the function of the sanitization in the door handle. The entire sanitization process may be processor driven and may be enabled by a protection circuit. The protection circuit may enable the function to perform sanitization in a manual manner.

Various embodiments of the self sanitizing door handle have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

It is noted that various connections are set forth between elements in the description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," Java, and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Although a few implementations have been described in detail above, other modifications are possible. Moreover, other mechanisms for performing the systems and methods described in this document may be used. In addition, the logic flows depicted in the figures may not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A self sanitizing door handle, said door handle comprising:
    a soft glass hollow membrane;
    one or more connectors;
    a central rod;
    a power unit that is a self-powered energy generation unit, wherein said self-powered energy generation unit comprises a spring and rail assembly with plurality of turbines; and
    a plurality of lights on said central rod inside said hollow membrane protectively covered by said one or more connectors in an active state of sanitization in said self sanitizing door handle.

2. The self sanitizing door handle as claimed in claim 1, further comprising a light indication unit configured to reflect a status of the plurality of lights inside said soft glass hollow membrane.

3. The self sanitizing door handle as claimed in claim 1, wherein said one or more connectors are interlocking connectors configured to act as a shield cover during a working state of said plurality of lights in said soft glass hollow membrane.

4. The self sanitizing door handle as claimed in claim 1, further comprising an outer covering of aluminium.

5. The self sanitizing door handle as claimed in claim 1, further comprising one or more sensors configured to detect presence of one or more users.

6. The self sanitizing door handle as claimed in claim 1, further comprising a control circuit for causing a UV-C disinfectant to be conveyed to the handle in intervals, wherein the intervals are responsive to an external condition and the control circuit if free of any manual activation.

7. A method of operating said self sanitizing door handle as claimed in any one of claims 1 and 2-6.

* * * * *